United States Patent
Karlsson et al.

(10) Patent No.: US 6,310,051 B1
(45) Date of Patent: Oct. 30, 2001

(54) USE OF CHELATING AGENTS IN THE TREATMENT OF ATHEROSCLEROTIC CONDITIONS

(75) Inventors: Jan Olof Gustav Karlsson, Nesoddtangen (NO); Rolf Goran Gustav Andersson, Vikingstad (SE); Anders Olsson, Vreta Kloster (SE); Bo Zieden, Norrkobing (SE); Per Jynge, Trondheim (NO); Tudor Griffith, Cardiff (GB); Derek Grant, Nittedal (NO); Robertson Towart, Stoke Poges (GB); Helge Refsum, Oslo (NO)

(73) Assignee: Nycomed Imaging AS, Olso (NO)

(*) Notice: Subject to any disclaimer, the term of this patent is extended or adjusted under 35 U.S.C. 154(b) by 0 days.

(21) Appl. No.: 09/599,861

(22) Filed: Jun. 23, 2000

Related U.S. Application Data

(63) Continuation of application No. PCT/GB98/03839, filed on Dec. 18, 1998.
(60) Provisional application No. 60/076,794, filed on Mar. 4, 1998.

(30) Foreign Application Priority Data

Dec. 23, 1997 (GB) .................................................. 9727224

(51) Int. Cl.$^7$ .................................................. A61K 31/675
(52) U.S. Cl. .......................... 514/85; 514/188; 514/346; 514/352; 514/354; 514/356; 514/191; 514/824
(58) Field of Search .......................... 514/89, 188, 345, 514/346, 352, 354, 356, 191, 824

(56) References Cited

U.S. PATENT DOCUMENTS 3,838,196   9/1974   Mercer .

FOREIGN PATENT DOCUMENTS

| 0 290 041 A | 11/1988 | (EP) . |
| 0 292 761 A | 11/1988 | (EP) . |
| 0 299 795 A | 1/1989 | (EP) . |
| 0 368 223 A | 5/1990 | (EP) . |
| 0 391 769 A | 10/1990 | (EP) . |

OTHER PUBLICATIONS

E. Olszewer; J.P. Carter: "EDTA Chelation Therapy in Chronic Degenerative Disease", Medical Hypotheses, Sep. 1988, XP002097971.

"EDTA Chelation therapy for Arteriosclerotic Heart Disease", Med. Lett, Drugs Ther., 1981, XP002097972.

*Primary Examiner*—James H. Reamer
(74) *Attorney, Agent, or Firm*—Bacon & Thomas, PLLC

(57) ABSTRACT

The invention provides the use of dipyridoxyl or aminopolycarboxylic acid based chelating agents, metal chelates and salts thereof, in the manufacture of a therapeutic agent for use in the treatment or prophylaxis of atherosclerosis and related conditions in the human or non-human animal body. Preferred compounds for use in the method of the invention are compounds of formula (I) or a metal chelate or salt thereof (wherein in formula (I) each $R^1$ independently represents hydrogen or —$CH_2COR^5$; $R^5$ represents hydroxy, optionally hydroxylated alkoxy, amino or alkylamido; each $R^2$ independently represents a group $XYR^6$; X represents a bond, or a $C_{1-3}$ alkylene or oxoalkylene group optionally substituted by a group $R^7$; Y represents a bond, an oxygen atom or a group $NR^6$; $R^6$ is a hydrogen atom, a group $COOR^8$, an alkyl, alkenyl, cycloalkyl, aryl or aralkyl group optionally substituted by one or more groups selected from $COOR^8$, $CONR^8_2$, $NR^8_2$, $OR^8$, $=R^8$, $=O$, $OP(O)(OR^8)R^7$ and $OSO_3M$; $R^7$ is hydroxy, an optionally hydroxylated, optionally alkoxylated alkyl or aminoalkyl group; $R^8$ is a hydrogen atom or an optionally hydroxylated, optionally alkoxylated alkyl group; M is a hydrogen atom or one equivalent of a physiologically tolerable cation, e.g. an alkali or alkaline earth cation, an ammonium ion or an organic amine cation, such as a meglumine ion; $R^3$ represents a $C_{1-8}$ alkylene group, preferably a $C_{1-6}$, e.g. a $C_{2-4}$ alkylene group, a 1,2-cycloalkylene group, or a 1,2-arylene group; each $R^4$ independently represents hydrogen or $C_{1-3}$ alkyl; and each $R^9$ independently may be absent or represents hydrogen, alkyl, hydroxyalkyl or carboxyalkyl).

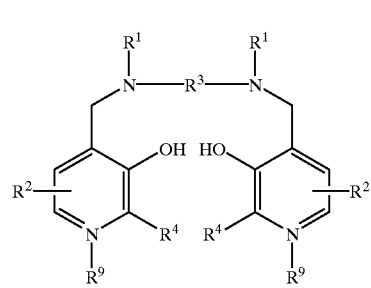

(I)

15 Claims, 3 Drawing Sheets

USE OF CHELATING AGENTS IN THE TREATMENT OF ATHEROSCLEROTIC CONDITIONS

This application is a continuation application of PCT/GB98/03839, filed Dec. 18, 1998, which is itself a continuation-in-part of U.S. provisional application No. 60/076,794, filed Mar. 4, 1998.

The present invention relates to the use of chelating agents and their metal chelates in medicine, in particular in treating or preventing atherosclerosis and related conditions.

It has been estimated that half of all deaths in Western countries result from atherosclerosis, a disease in which cholesterol-rich "foam cells" accumulate and form plaques in arterial walls, obstructing blood flow, which ultimately leads to heart attack or stroke.

It has been found that elevated lipoprotein concentration in plasma accelerates the development of atherosclerosis. Recent research has shown oxidative modification of low density lipoprotein (LDL) to be an early and important event in the development of atherosclerosis (Steinberg et al, N Engl J Med 320: 915, 1989).

The precursors of atherosclerotic foam cells are predominantly circulating monocytes and macrophages and it has been found that the cholesterol content of these foam cells increases upon interaction with oxidatively modified forms of low density lipoproteins (Palinski et al, Proc Natl Acad Sci 86: 1372, 1986; Montgomery et al, Proc Natl Acad Sci 83: 6631, 1986). It is well known that the redox-active transition metals iron and copper enhance LDL oxidation, probably through a process involving superoxide radicals, and thus, these ions are believed to be of importance in the initiation of atherosclerosis. It is envisaged that oxidation of LDL occurs by a mechanism similar to that seen in membranes during ischaemia-reperfusion and anthracycline toxicity with superoxide, where iron and copper serve central, catalytic roles (see Ryan & Aust, Crit Rev Toxicol 22: 119, 1992).

Oxidation of LDL results, among other things, in an impaired nitric oxide-dependent vasorelaxation (Kugiyama et al, Nature 344: 160, 1990). The impaired nitric oxide-dependent vasorelaxation may, in turn, cause hypertension, which by itself is one of the primary risk factors for cardiovascular diseases in humans. The impaired vasorelaxation may be due to inactivation of nitric acid by superoxide.

It will be appreciated that there thus exists a continuing need for compounds which are able to treat or prevent atherosclerosis, for example by inhibiting LDL oxidation.

The medical use of chelating agents and their metal chelates is well established, for example in diagnostic techniques such as X-ray, magnetic resonance imaging (MRI), ultrasound imaging or scintigraphy. A wide variety of chelating agents and metal chelates are known or have been described.

Aminopoly (carboxylic acid or carboxylic acid derivative) chelating agents and their metal chelates are well known and are described for example in EP-A-299795, EP-A-71564, DE-A-3401052, EP-A-203962 and EP-A-436579.

Dipyridoxyl based chelating agents and their chelates with trivalent metals have been described by Taliaferro (Inorg. Chem. 23: 1183–1192 (1984)). The compound N,N'-dipyridoxyl ethylenediamine-N,N'-diacetic acid (PLED) has been evaluated as a chelating agent for the preparation of gallium or indium containing radiopharmaceuticals (see Green et al. Int. J. Nucl. Med. Biol, 12(5): 381–386 (1985)).

A number of PLED derivatives and analogues have also been described for use in MRI contrast media, in particular the chelating agent N,N'-bis-(pyridoxal-5-phosphate)-ethylenediamine-N,N'-diacetic acid (DPDP) and its manganese (II) chelate, Mn DPDP (see EP-A-290047 and EP-A-292761).

We have now found that certain chelating agents, in particular dipyridoxyl and aminopolycarboxylic acid based chelating agents, and their metal chelates are particularly effective in treating or preventing atherosclerosis and related conditions.

In one aspect the invention thus provides the use of a dipyridoxyl or aminopolycarboxylic acid based chelating agent, or a metal chelate or salt thereof, in the manufacture of a therapeutic agent for use in the treatment or prophylaxis of atherosclerosis and related conditions in the human or non-human animal body.

In a further aspect the invention provides the use of a compound of formula I

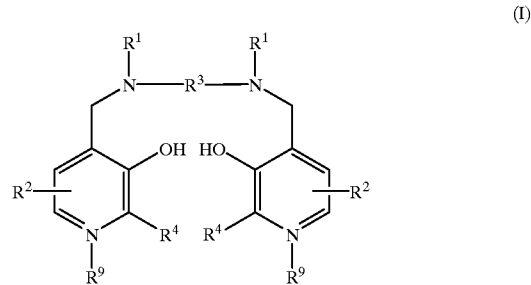

(I)

or a metal chelate or salt thereof in the manufacture of a therapeutic agent for use in the treatment or prophylaxis of atherosclerosis and related conditions in the human or non-human animal body (wherein in formula I each $R^1$ independently represents hydrogen or —$CH_2COR^5$;

$R^5$ represents hydroxy, optionally hydroxylated alkoxy, amino or alkylamido;

each $R^2$ independently represents a group $XYR^6$;

X represents a bond, or a $C_{1-3}$ alkylene or oxoalkylene group optionally substituted by a group $R^7$;

Y represents a bond, an oxygen atom or a group $NR^6$;

$R^6$ is a hydrogen atom, a group $COOR^8$, an alkyl, alkenyl, cycloalkyl, aryl or aralkyl group optionally substituted by one or more groups selected from $COOR^8$, $CONR^8{}_2$, $NR^8{}_2$, $OR^8$, $=NR^8$, $=O$, $OP(O)(OR^8)R^7$ and $OSO_3M$;

$R^7$ is hydroxy, an optionally hydroxylated, optionally alkoxylated alkyl or aminoalkyl group;

$R^8$ is a hydrogen atom or an optionally hydroxylated, optionally alkoxylated alkyl group;

M is a hydrogen atom or one equivalent of a physiologically tolerable cation, e.g. an alkali or alkaline earth cation, an ammonium ion or an organic amine cation, such as a meglumine ion;

$R^3$ represents a $C_{1-8}$ alkylene group, preferably a $C_{1-6}$, e.g. a $C_{2-4}$ alkylene group, a 1,2-cycloalkylene group, or a 1,2-arylene group;

each $R^4$ independently represents hydrogen or $C_{1-3}$ alkyl; and each $R^9$ independently may be absent or represents hydrogen, alkyl, hydroxyalkyl or carboxyalkyl).

In another aspect the invention provides a method of treatment of the human or non-human animal body to combat or prevent atherosclerosis and related conditions, said method comprising administering to said body an effective amount of a chelating agent selected from dipyridoxyl and aminopolycarboxylic acid based chelating agents and metal chelates and salts thereof, preferably a compound of formula I or a metal chelate or salt thereof.

Related conditions to atherosclerosis include conditions such as hypertension which can be treated indirectly by the prevention of atherosclerosis or alternatively, directly since it is envisaged that the inhibiton of the oxidation of LDL may alleviate impaired nitric-oxide dependent vasorelaxation.

Also, it is envisaged that the compounds according to the invention may be useful in cytotoxic antimicrobial treatment, e.g. to combat infections associated with bacteria, protozoa, parasites etc. Protozoal infections which may be treated using the compounds of the invention include malaria, e.g. *Plasmodium falciparium* and *Pneumocystis carinii*, trypanosomiasis (Chagas' disease) and leichmaniasis. Methods of metal detoxification are also envisaged using the compounds of the invention. For example, these may be used to treat iron intoxication such as in thalassemia.

Other chelators suitable for use in the method of the invention include the macrocyclic and more preferably linear or branched aminopolycarboxylic acid chelants of EP-A-299795, EP-A-71564, DE-A-3401052, EP-A-203962, EP-A-436579 and the phosphorus oxyacid analogs. Preferred chelating agents include amides of DTPA and EDTA in which the nitrogens of the amide groups may be substituted by one or more $C_{1-18}$ alkyl groups, e.g. DTPA.BMA and EDTA.BMA.

As used herein the terms "alkyl" and "alkylene" include both straight-chained and branched, saturated and unsaturated hydrocarbons. The term "1,2-cycloalkylene" includes both cis and trans cycloalkylene groups and alkyl substituted cycloalkylene groups having from 5–8 carbon atoms. The term "1,2-arylene" includes phenyl and napthyl groups and alkyl substituted derivatives thereof having from 6 to 10 carbon atoms.

Unless otherwise specified, any alkyl, alkylene or alkenyl moiety may conveniently contain from 1 to 20, preferably 1–8, more preferably 1–6 and especially preferably 1–4 carbon atoms.

Cycloalkyl, aryl and aralkyl moieties may conveniently contain 3–18, preferably 5–12 and especially preferably 5–8 ring atoms. Aryl moieties comprising phenyl or naphthyl groups are preferred. As aralkyl groups, phenyl $C_{1-3}$ alkyl, especially benzyl, are preferred.

Where groups may optionally be substituted by hydroxy groups, this may be monosubstitution or polysubstitution and, in the case of polysubstitution, alkoxy and/or hydroxy substituents may be carried by alkoxy substituents.

In formula I, $R^5$ is preferably hydroxy, $C_{1-8}$ alkoxy, ethylene glycol, glycerol, amino or $C_{1-8}$ alkylamido. Preferably each group $R^1$ represents —$CH_2COR^5$ in which $R^5$ is hydroxy.

In the compounds of formula I, X is preferably a bond or a group selected from $CH_2$, $(CH_2)_2$, CO, $CH_2CO$, $CH_2CH_2CO$ or $CH_2COCH_2$. Preferably, Y represents a bond.

The compounds of formula I may have the same or different $R^2$ groups on the two pyridyl rings and these may be attached at the same or different ring positions. However, it is especially preferred that substitution be at the 5- and 6-positions, most especially the 6-position, i.e. para to the hydroxy group. Compounds in which the $R^2$ groups are identical and identically located, e.g. 6,6', are especially preferred.

Preferred as groups $R^6$ are mono- or poly(hydroxy or alkoxylated) alkyl groups or a group of the formula $OP(O)(OR^8)R^7$.

$R^7$ is preferably hydroxy or an unsubstituted alkyl or aminoalkyl group.

The compounds of formula I may have the same or different $R^9$ groups on the two pyridyl rings, preferably the same, and preferably $R^9$ represents hydrogen, carboxymethyl or $R^9$ is absent.

Particularly preferred identities for group $R^2$ include $CHR^7OCO(CH_2)_xPh$ and $CHR^7OCO(CH_2CO)_xPh$ (wherein x is 1 to 3), $CHR^7OCOBu^t$, $CH_2N(H)R^{6'}$, $CH_2N(R^{6'})_2$, $N(H)R^{6'}$, $N(R^{6'})_2$, $CH_2OH$, $CH_2OR^{6'}$, $COOR^{6'}$, $CON(H)R^{6'}$, $CON(R^{6'})_2$ or $OR^{6'}$ (where $R^{6'}$ is a mono- or polyhydroxylated, preferably $C_{1-4}$, especially preferably $C_{1-3}$, alkyl group), $(CH_2)_nCOOR^{7'}$ (wherein n is 1 to 6), $COOR^{7'}$ (where $R^{7'}$ is a $C_{1-4}$ alkyl, preferably $C_{1-3}$, especially preferably a methyl group), $CH_2OSO_3^-M$, $CH_2CH_2COOH$, $CH_2OP(O)(OH)(CH_2)_3NH_2$, $CH_2OP(O)(OH)CH_3$ or $CH_2OP(O)(OH)_2$ group). Yet more preferably, $R^2$ represents a group of the formula $CH_2OP(O)(OH)_2$.

Compounds of formula I in which $R^3$ is ethylene and $R^2$ has any of the identities listed above are particularly preferred.

Preferred metal chelates of the compounds for use in the method of the invention are those in which the metal ions are selected from the alkali and alkaline earth metals and from those metals having an atomic number from 22–31, 42, 44 and 58–70 and more particularly chelates having a $K_a$ in the range from $10^9$ to $10^{25}$, preferably $10^{10}$ to $10^{24}$, more preferably $10^{11}$ to $10^{23}$, e.g. $10^{12}$ to $10^{22}$. Particularly preferred chelates are those with metals other than iron which have a $K_a$ value smaller, preferably by a factor of at least $10^3$, than the $K_a$ value of the corresponding iron ($Fe^{3+}$) chelate. Suitable ions include $Na^+$, $Mn^{2+}$, $Ca^{2+}$, $Zn^{2+}$, $Gd^{3+}$ and $Mg^{2+}$. $Mn^{2+}$ is especially preferred.

As chelates of aminopolycarboxylic acids, Mn DTPA.BMA and Mn EDTA.BMA are particularly preferred for use in accordance with the invention.

More particularly preferred for use in accordance with the invention are the compounds N,N'-bis-(pyridoxal-5-phosphate)-ethylenediamine-N,N'-diacetic acid or N,N'-bis(3-hydroxy-2-methyl-5-phosphonomethyl-4-pyridyl-methyl)-ethylenediamine-N,N'-diacetic acid (DPDP) and the manganese (II) chelate, Mn(DPDP), trisodium trihydrogen [[N,N'-ethylenebis[N-[[3-hydroxy-5-(hydroxymethyl)-2-methyl-4-pyridyl]methyl]glycine] 5,5'-bis(phosphato)] (8-)] manganate(6-) (MnDPDP trisodium salt), disodium dihydrogen [[N,N'-ethylenebis [N- [[3-hydroxy-5-(hydroxymethyl)-2-methyl-4-pyridylimethyl]glycine] 5-(phosphato)] (6-)] manganate (4-)(MnDPMP disodium salt), dihydrogen [N,N'-ethylenebis [N-[[3-hydroxy-5-(hydroxymethyl)-2-methyl-4-pyridyl]methyl] glycinato] (4-)] manganate(2-) (MnPLED) hexahydrogen [[N,N'-ethylene-N-[[3-hydroxy-5-(hydroxymethyl)-2-methyl-4-pyridyl]methyl]glycine]-N'-[[3-hydroxy-5-(hydroxymethyl)-2-methyl-4-(1 -carboxymethyl) pyridyl]methyl]glycine] 5,5'-bis(phosphato)](9-)] manganate(7-) (MnDPDP MOA), trisodium trihydrogen [[N,N'-ethylenebis [N-[[3-hydroxy-5-(hydroxymethyl)-2-methyl-4-(1-carboxymethyl)pyridyl]methyl]glycine] 5,5'-bis (phosphato)](8-)] manganate(6-) (MnDPDP DOA), disodium trihydrogen [[N,N'-ethylenebis[N-[[3-hydroxy-5-(hydroxymethyl)-2-methyl-4-pyridyl]methyl]glycine] 5,5'-bis(phosphato)](8-)] manganate(5-) (Mn(III)DPDP disodium salt), disodium trihydrogen [[N,N'-ethylenebis[N-[[3-hydroxy-5-(hydroxymethyl)-2-methyl-4-pyridyl]methyl] glycine] 5,5'-bis(phosphato)] (8-)] aluminide(5-) (AlDPDP disodium salt).

If not all of the labile hydrogens of the chelates are substituted by the complexed metal ion, biotolerability and/ or solubility of the chelate may be increased by substituting the remaining labile hydrogen atoms with physiologically biocompatible cations of inorganic and/or organic bases or amino acids. Examples of suitable inorganic cations include Li$^+$, K$^+$, Na$^+$ and especially Ca$^{2+}$. Suitable organic cations include ammonium, substituted ammonium, ethanolamine, diethanolamine, morpholine, glucamine, N,N,-dimethyl glucamine, lysine, arginine or ornithine.

The chelating agents and the metal chelates thereof for use in accordance with the invention are particularly effective in the treatment or prevention of atherosclerosis and related conditions.

The compounds of the invention may be administered along with other conventional antiatherosclerotic agents including ciprofibrate and statins such as simvastatin, pravastatin and fluvaststin and this forms a further aspect of the invention. It is envisaged that a combination of antiatherosclerotic agents may act synergistically together.

Thus viewed from a still yet further aspect, the invention provides a pharmaceutical composition comprising a chelating agent according to the invention or a metal chelate or salt thereof, together with one or more antiatherosclerotic agents and at least one pharmaceutically acceptable carrier or excipient.

The compounds of the invention may be prepared by methods known in the art. Suitable methods for preparing the amino polycarboxylic acid based chelating agents are described in EP-A-299795, EP-A-71564, DE-A-3401052, EP-A-203962 and EP-A-436579.

In preparing the dipyridoxyl compounds, the compound PLED may be used as a starting material and may be appropriately derivatised using conventional procedures to obtain the compounds of formula I.

Suitable methods for preparing the compounds of formula I are described for example in EP-A-290047.

Alternatively the compounds of formula I may be prepared by reacting the corresponding pyridoxal compound with an alkylene diamine according to the procedure for making PLED described by Taliaferro (supra).

Alternatively, the compounds in accordance with the invention may be prepared by a process comprising one or more of the following steps:

(a) reacting a compound of formula II

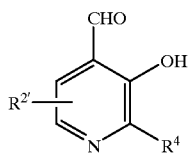
(II)

with a diamine of formula (III)

(III)

(wherein R$^3$ and R$^4$ are as hereinbefore defined and R$^{2'}$ is an optionally protected group R$^2$ as hereinbefore defined)

(b) hydrogenating a compound of formula (IV) obtained in step (a)

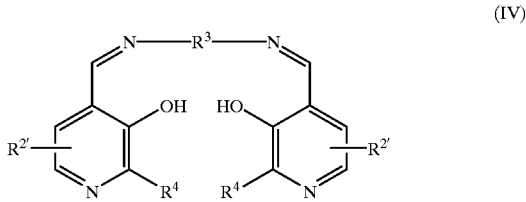
(IV)

(wherein R$^3$, R$^4$ and R$^{2'}$ are as hereinbefore defined)

(c) reacting a compound of formula (V)

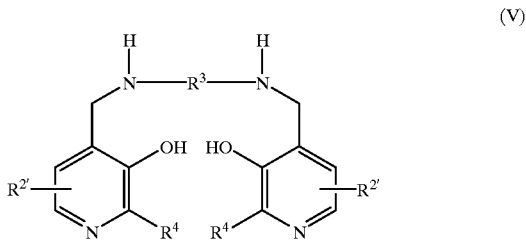
(V)

(wherein R$^3$, R$^4$ and R$^{2'}$ are as hereinbefore defined) with a haloacetic, preferably bromoacetic, acid, and if necessary removing any protecting groups used;

(d) reacting a compound of formula (V) or formula (I) (where R$^9$ groups are absent) with a reagent serving to introduce an R$^9$ group at a pyridyl nitrogen, e.g. a compound R$^9$Lv where Lv is a leaving group; and (e) converting a compound of formula I into a chelate complex or salt thereof.

Pyridoxyl phosphate, pyridoxal and the other compounds of formula II and the alkylene diamine, cycloalkylene diamine and arylene compounds of formula III are well-known compounds readily available or can be readily synthesised by procedures well known in the art.

The reaction of step (a) may conveniently be performed in a suitable solvent, such as an alcohol (e.g. methanol) at a temperature in the range of from 0 to 60° C.

To obtain compounds of formula I where the R$^2$ groups are the same, a diamine of formula III may be reacted with two molar equivalents of a compound of formula II. For the preparation of compounds of formula I where the R$^2$ groups are different, the diamine of formula III is first reacted with a first compound of a formula II having a desired R$^{2'}$ group, and the reaction product thereby obtained is then reacted with a second compound of formula II bearing a different R$^{2'}$ group.

The hydrogenation of step (b) may be performed using conventional procedures, e.g. using a palladium or platinum catalyst.

The metal chelates for use in accordance with the invention may be formed by conventional procedures known in the art. In general, such processes involve dissolving or suspending a metal oxide or metal salt (e.g. nitrate, chloride or sulfate) in water or a lower alcohol such as methanol, ethanol, or isopropanol. To this solution or suspension is added an equimolar amount of the chelating agent in water or a lower alcohol and the mixture is stirred, if necessary with heating moderately or to the boiling point, until the reaction is completed. If the chelate salt formed is insoluble in the solvent used, the reaction product is isolated by filtering. If it is soluble, the reaction product is isolated by evaporating to dryness, e.g. by spray drying or lyophilising.

If acid groups such as the phosphoric acid groups are still present in the resulting chelate, it is advantageous to convert the acidic chelate salt into a neutral chelate salt by reaction with inorganic and/or organic bases or amino acids, which form physiologically acceptable cations, and to isolate them.

The carboxylic and phosphoric acid groups of the chelating agents can also be neutralised by esterification to prepare carboxylate and phosphate esters. Such esters can be prepared from the corresponding alcohols by conventional procedures known in the art. Suitable esters include, for example, esters of straight-chained or branched alcohols having from 1 to 18 carbon atoms, mono and polyhydric alkyl amino alcohols having from 1 to 18 carbon atoms, preferably having from 1 to 6 carbons, such as serinol or diethanolamine, and polyhydric alcohols having from 1 to 18 carbon atoms, such as ethylene glycol or glycerol.

Where the metal chelate carries an overall charge it will conveniently be used in the form of a salt with a physiologically acceptable counterion, for example an ammonium, substituted ammonium, alkali metal or alkaline earth metal (e.g. calcium) cation or an anion deriving from an inorganic or organic acid. In this regard, meglumine salts are particularly preferred.

The therapeutic agents of the present invention may be formulated with conventional pharmaceutical or veterinary formulation aids, for example stabilizers, antioxidants, osmolality adjusting agents, buffers, pH adjusting agents, lubricating agents, wetting agents, emulsifying agents, suspending agents, preserving agents, sweetening agents etc. Administration may be by any suitable method known in the art, including for example oral, parenteral (e.g. intramuscular, subcutaneous, intraperitoneal or intravenous), rectal or topical administration. Thus the agent of the present invention may be in a conventional pharmaceutical administration form such as a tablet, capsule, powder, solution, suspension, dispersion, syrup, suppository, etc. However, solutions, suspensions and dispersions in physiologically acceptable carrier media, for example water for injections, will generally be preferred.

The compounds according to the invention may therefore be formulated for administration using physiologically acceptable carriers or excipients in a manner well-known to those skilled in the art. For example, the compounds, optionally with the addition of pharmaceutically acceptable excipients, may be suspended or dissolved in an aqueous medium, with the resulting solution or suspension then being sterilized. Suitable additives include, for example, physiologically biocompatible buffers (e.g. tromethamine hydrochloride), additions (e.g. 0.01 to 10 mole percent) of chelants (such as, for example, DTPA, DTPA-bisamide or non-complexed chelants of formula I) or calcium chelate complexes (e.g. calcium DTPA, CaNaDTPA-bisamide, calcium salts or chelates of chelants of formula I), or, optionally, additions (e.g. 1 to 50 mole percent) of calcium or sodium salts (e.g. calcium chloride, calcium ascorbate, calcium gluconate or calcium lactate combined with metal chelate complexes of chelating agents according to the invention and the like).

If the compounds are to be formulated in suspension form, e.g., in water or physiological saline for oral administration, a small amount of soluble chelate may be mixed with one or more of the inactive ingredients traditionally present in oral solutions and/or surfactants and/or aromatics for flavouring.

The preferred mode for administering the metal chelates in accordance with the invention is peroral. Due to its higher lipophilicity in comparison to DPDP, the desphosphorylated form of metallo-DPDP, i.e. PLED is particularly suitable for oral administration.

If the compounds of the invention are to be administered parenterally, e.g. intravenous solutions, these should be sterile and free from physiologically unacceptable agents, and should have low osmolality to minimize irritation or other adverse effects upon administration, and thus the compositions should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487. (1975) and The National Formulary XIV, 14th ed. Washington: American Pharmaceutical Association (1975). The solutions may contain preservatives, antimicrobial agents, buffers and antioxidants conventionally used for parenteral solutions, excipients and other additives which are compatible with the chelates and which will not interfere with the manufacture, storage or use of the products.

The therapeutic agent in accordance with the invention, if in solution, suspension or dispersion form, will generally contain the chelant or metal chelate at a concentration in the range of from 0.0001 to 5.0 moles per litre, preferably 0.01 to 0.1 moles per litre. If convenient, the therapeutic agent may however be supplied in a more concentrated form for dilution prior to administration.

The therapeutic agent in accordance with the invention may conveniently be administered in amounts of from $10^{-2}$ to 1000 µmol of the compounds per kilogram of body weight, e.g. about 100 µmol per kg bodyweight.

The present invention will now be illustrated further by the following non-limiting Examples and with reference to the attached figures, in which.

EXAMPLE 1

The protective effect of MnDPDP and MnPLED against oxidation of human LDL was assayed in vitro. Copper-catalyzed LDL-oxidation was monitored by following the increase in absorbance at wavelength 234 nm over time (representing increase in diene-products).

Method

Human LDL (1.025<d<1.050 g/ml) was freshly isolated (from sera of normolipidemic donors who had fasted overnight) by sequential ultracentrifugation, in the presence of EDTA (1.4 mg/ml) to inihibit lipid peroxidation. LDL was finally dialyzed under nitrogen against 10 mM phosphate buffer with 160 mM NaCl, pH 7.4 (PBS), for 24 h at 4° C.

Assays were performed at 30° C. in PBS by mixing 200 µl of the LDL-containing dialysate to PBS to a final volume of 2000 µl. The LDL-oxidation was started by adding 5 µM CuCl$_2$ and the changes in absorbance at wavelength 234 nm was followed over 225 minutes.

Results

Figure 1:
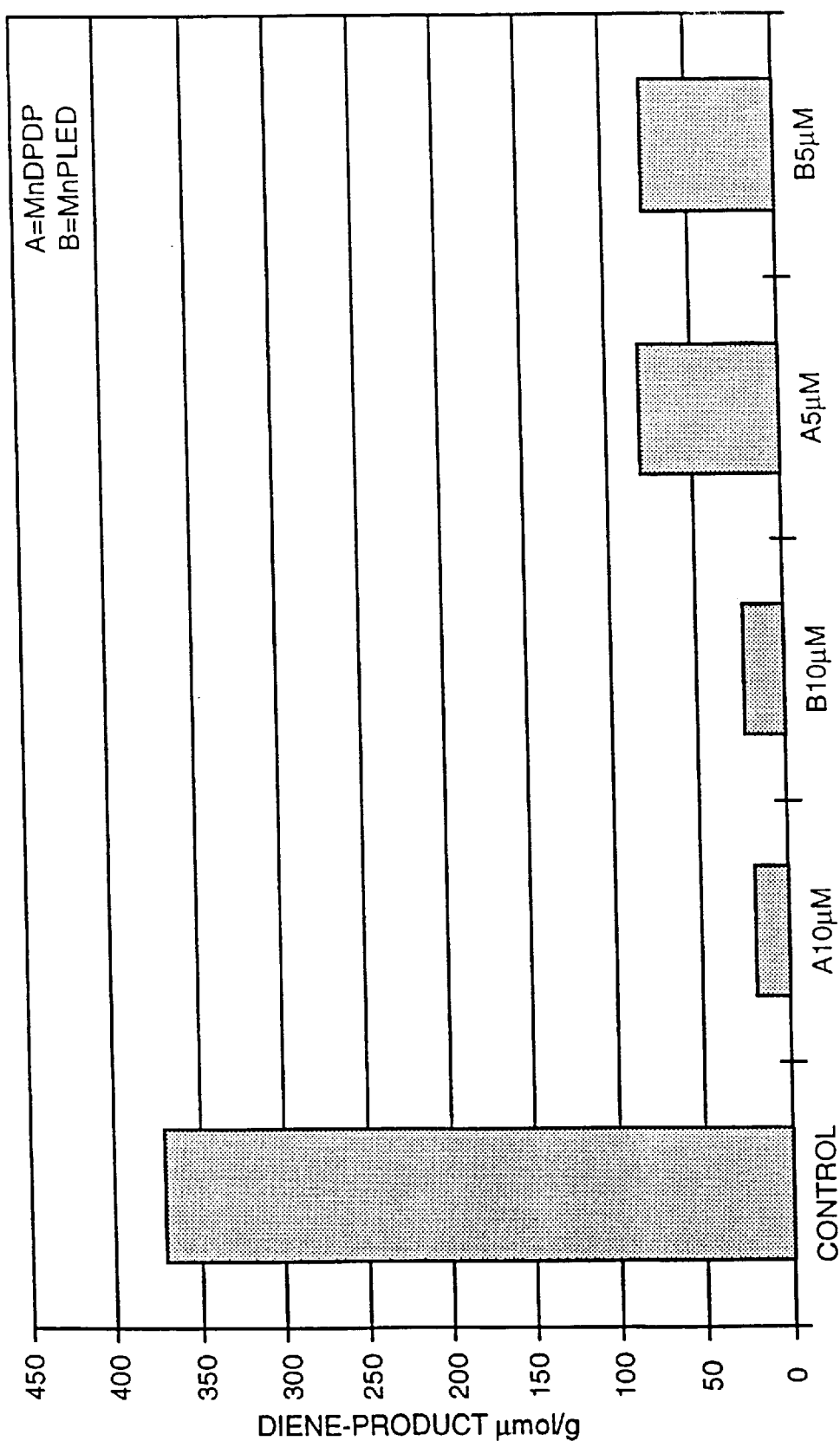
FIGS. 1 and 2 illustrate the inhibition of LDL oxidation by different concentrations of MnDPDP and MnPLED.
Figure 2:
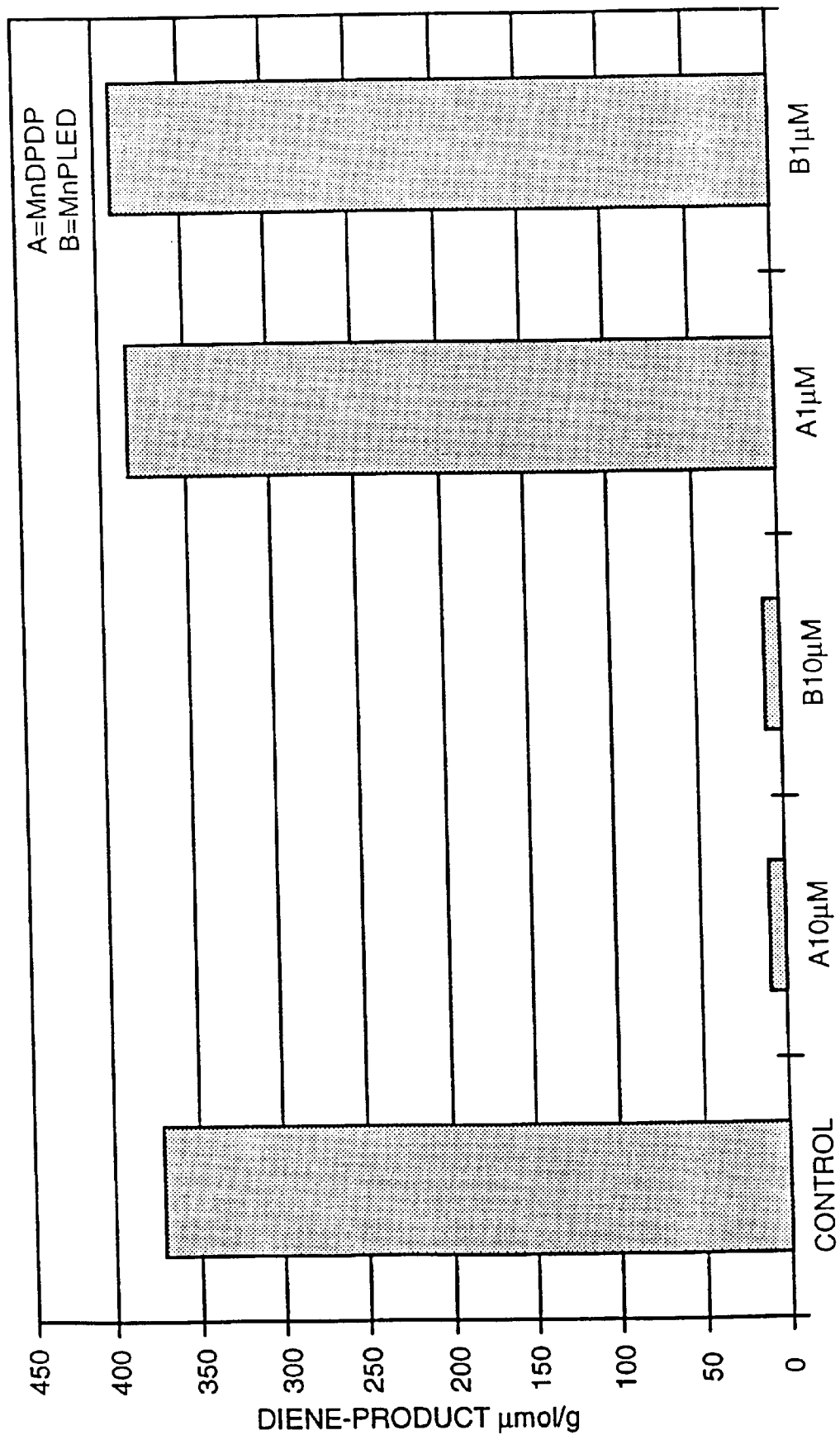

Typical results are shown in FIGS. 1 and 2 attached hereto.

It can be seen that MnDPDP and MnPLED inhibited LDL oxidation in a concentration-dependent manner. An almost complete inhibition was seen at 10 µM, whereas 5 µM gave rise to more than 50% inhibition.

It is clear from FIGS. 1 and 2 that MnDPDP and MnPLED unexpectedly inhibits LDL oxidation.

EXAMPLE 2

In order to get a rough estimate of the bioavailability of MnPLED after oral administration, rats were instilled with MnPLED into the stomach and the plasma concentrations of metallo-PLED was determined at various times after administration.

Method

100 $\mu$mol/kg MnPLED was instilled into the stomach. Blood (ca 4.5 ml) was withdrawn by cardiac puncture (under $CO_2$-anaesthesia) and collected in tubes containing heparin (trace metal analysis tubes), 5, 30, 60, 120 minutes and 24 hours after oral administration (2 rats for each time point). Plasma was prepared by centrifugation and ultrafiltration and metallo-PLED was determined by HPLC as described by Toft et al. 1997 (Acta Radiologica 38: 677–689).

Results

Figure 3:
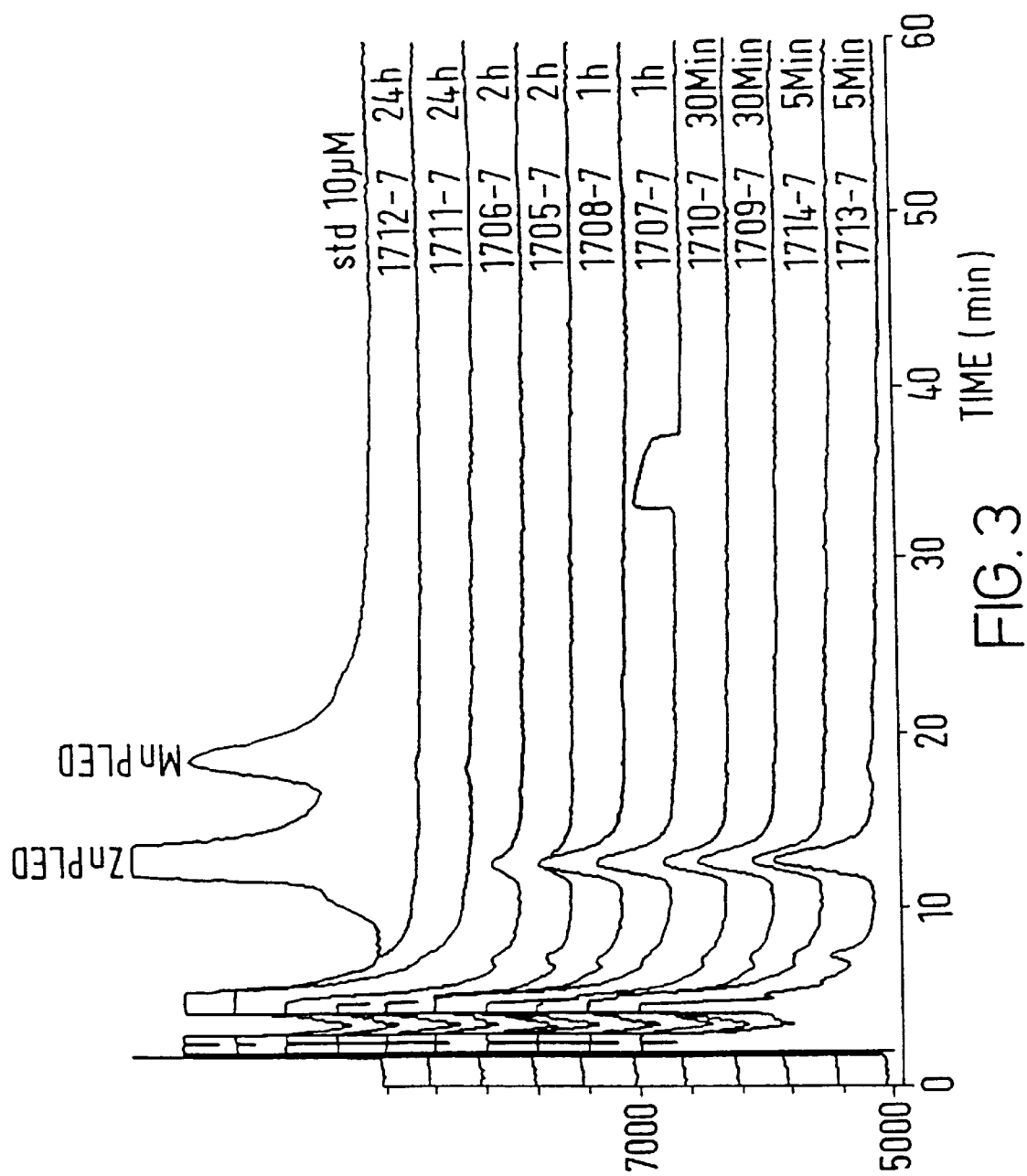
FIG. 3 shows a HPLC chromatogram illustrating peroral uptake after peroral administration of MnPLED.

Typical results are shown in FIG. 3 attached hereto.

From the HPLC chromatograms (FIG. 3) it can be seen that ZnPLED is already present in plasma 5 minutes after administration. The concentration of ZnPLED in plasma corresponds to approximately 1 $\mu$M. Although the chromatogram at 5 minutes after administration in one animal may indicate the presence of small amounts of MnPLED in plasma, most of the MnPLED has already been transmetallated into ZnPLED. Such a transmetallation is well characterised upon intravenous administration (Toft et al., 1997).

It is evident that MnDPDP is absorbed into the blood stream at peroral administration.

What is claimed is:

1. A method of treatment of the human or non-human animal body to combat or prevent atherosclerosis and related conditions, said method comprising administering to said body an effective amount of a dipyridoxyl based chelating agent, or a metal chelate or salt thereof.

2. Method as claimed in claim 1 wherein said chelating agent is a compound of formula I:

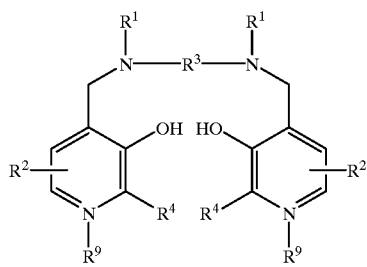

(I)

(wherein in formula I each $R^1$ independently represents hydrogen or —$CH_2COR^5$;

$R^5$ represents hydroxy, optionally hydroxylated alkoxy, amino or alkylamido;

each $R^2$ independently represents a group $XYR^6$;

X represents a bond, or a $C_{1-3}$ alkylene or oxoalkylene group optionally substituted by a group $R^7$;

Y represents a bond, an oxygen atom or a group $NR^6$;

$R^6$ is a hydrogen atom, a group $COOR^8$, an alkyl, alkenyl, cycloalkyl, aryl or aralkyl group optionally substituted by one or more groups selected from $COOR^8$, $CONR^8{}_2$, $NR^8{}_2$, $OR^8$, =$NR^8$, =O, OP(O) $(OR^8)R^7$ and $OSO_3M$;

$R^7$ is hydroxy, an optionally hydroxylated, optionally alkoxylated alkyl or aminoalkyl group;

$R^8$ is a hydrogen atom or an optionally hydroxylated, optionally alkoxylated alkyl group;

M is a hydogen atom or one equivalent of a physiologically tolerable cation;

$R^3$ represents a $C_{1-8}$ alkylene group, a 1,2-cycloalkylene group, or a 1,2-arylene group;

each $R^4$ independently represents hydrogen or $C_{1-3}$ alkyl; and each $R^9$ independently may be absent or represents hydrogen, alkyl, hydroxyalkyl or carboxyalkyl) or a metal chelate or salt thereof.

3. Method as claimed in claim 2 wherein in formula I:

$R^1$ represents —$CH_2COR^5$ in which $R^5$ is hydroxy;

X is a bond or a group selected form $CH_2$, $(CH_2)_2$, CO, $CH_2CO$, $CH_2CH_2CO$ or $CH_2COCH_2$;

Y is a bond;

$R^6$ is a mono- or ploy (hydroxy or alkoxylated) alkyl group or a group of the formula OP(O) $(OR^8)$ $R^7$;

$R^7$ is hydroxy or an unsubstituted alkyl or aminoalkyl group;

$R^3$ is ethylene; and $R^9$ is hydrogen, carboxymethyl or is absent.

4. Method as claimed in claim 1 wherein said metal chelate comprises a metal ion selected from the group consisting of the alkali and alkaline earth metals and metals having an atomic number of from 22–31, 42, 44 and 58–70.

5. Method as claimed in claim 4 wherein said metal chelate has a $K_a$ in the range of from $10^9$ to $10^{25}$.

6. Method as claimed in claim 4 wherein said metal chelate has a $K_a$ in the range of from $10^{12}$ to $10^{22}$.

7. Method as claimed in claim 4 wherein said metal chelate has a $K_a$ value smaller by a factor of at least $10^3$ than the $K_a$ value of the corresponding iron ($Fe^{3+}$) chelate.

8. Method as claimed in claim 4 wherein said metal ion is selected from the group consisting of $Na^+$, $Mn^{2+}$, $Ca^{2+}$, $Zn^{2+}$, $Gd^{3+}$ and $Mg^{2+}$.

9. Method as claimed in claim 4 wherein said chelating agent is a compound selected from N,N'-bis-(pyridoxal-5-phosphate)-ethylenediamine-N,N'-diacetic acid or N,N'-bis (3-hydroxy-2-methyl-5-phosphonomethyl-4-pyridyl-methyl)-ethylenediamine-N,N'-diacetic acid (DPDP) and the manganese (II) chelate, Mn(DPDP), trisodium trihydrogen [[N,N'-ethylenebis[N-[[3-hydroxy-5-(hydroxymethyl)-2-methyl-4-pyridyl]methyl]glycine] 5,5'-bis(phosphato)] (8-)] manganate(6-) (MnDPDP trisodium salt), disodium dihydrogen [[N,N'-ethylenebis[N-[[3-hydroxy-5-(hydroxymethyl)-2-methyl-4-pyridyl]methyl]glycine] 5-(phosphato)](6-)]manganate (4-) (MnDPMP disodium salt), dihydrogen [N,N'-ethylenebis[N-[[3-hydroxy-5-(hydroxymethyl)-2-methyl-4-pyridyl]methyl] glycinato] (4-)] manganate (2-) (MnPLED), hexahydrogen [[N,N'-ethylene-N-[[3-hydroxy-5-(hydroxymethyl)-2-methyl-4-pyridyl]methyl]glycine] -N'-[[3-hydroxy-5-(hydroxymethyl)-2-methyl-4-(1-carboxymethyl) pyridyl] methyl]glycine] 5,5'-bis(phosphato)] (9-)] manganate (7-) (MnDPDP MOA), trisodium trihydrogen [[N,N'-ethylenebis [N-[[3-hydroxy-5-(hydroxymethyl)-2-methyl-4-(1-carboxymethyl) pyridyl]methyl]glycine] 5,5'-bis (phosphato)] (8-)] manganate (6-) (MnDPDP DOA), disodium trihydrogen [[N,N'-ethylenebis[N-[[3-hydroxy-5-(hydroxymethyl)-2-methyl-4-pyridyl]methyl]glycine] 5,5'-bis (phosphato)] (8-)] manganate (5-) (Mn(III)DPDP disodium salt), and disodium trihydrogen [[N,N'-ethylenebis[N-[[3-hydroxy-5-(hydroxymethyl)-2-methyl-4-pyridyl]methyl]glycine] 5,5'-bis(phosphato)](8-)] aluminide (5-)_(A1DPDP disodium salt).

10. Method as claimed in claim 1 wherein said metal chelate is a manganese (II) chelate of N,N'-bis-(pyridoxal-5-phosphate)-ethylenediamine-N,N'-diacetic acid (DPDP) or of N,N'-dipyridoxyl ethylenediamine-N,N'-diacetic acid (PLED).

11. Method as claimed in claim 1 wherein the condition treated is hypertension, trypanosomiasis (Chagas' disease), leichmaniasis, pneumocystosis or thalassemia, or conditions associated with Plasmodium falciparium.

12. A pharmaceutical composition comprising a chelating agent, or a metal chelate or salt thereof, as defined in claim 1, together with at least one anti-atherosclerotic agent and at least one pharmaceutically acceptable carrier or excipient.

13. A composition as claimed in claim 12 wherein said anti-atherosclerotic agent is selected from the group consisting of ciprofibrate, simvastatin, pravastatin, flurastatin or a mixture thereof.

14. A pack containing a chelating agent, or a metal chelate or salt thereof, as defined in claim 1, and separately an anti-atherosclerotic agent for simultaneous, separate or sequential use in a method of treating atherosclerosis or a related condition.

15. A pack as claimed in claim 14 wherein said anti-atherosclerotic agent is selected from the group consisting of ciprofibrate, simvastatin, pravstatin, flurastatin or a mixture thereof.

* * * * *